(12) United States Patent
Im et al.

(10) Patent No.: US 10,428,458 B2
(45) Date of Patent: Oct. 1, 2019

(54) MEDICAL NONWOVEN FABRIC, AND PREPARATION METHOD THEREOF

(71) Applicant: KOREA INSTITUTE OF INDUSTRIAL TECHNOLOGY, Chungcheongnam-do (KR)

(72) Inventors: Jung Nam Im, Gyeonggi-do (KR); Dae Young Lim, Gyeonggi-do (KR); Guk-Hwan An, Gyeongsangbuk-do (KR); Yoon Jin Kim, Gyeonggi-do (KR)

(73) Assignee: KOREA INSTITUTE OF INDUSTRIAL TECHNOLOGY (KR)

(*) Notice: Subject to any disclaimer, the term of this patent is extended or adjusted under 35 U.S.C. 154(b) by 659 days.

(21) Appl. No.: 15/016,810

(22) Filed: Feb. 5, 2016

(65) Prior Publication Data

US 2016/0153143 A1   Jun. 2, 2016

Related U.S. Application Data

(62) Division of application No. 13/517,356, filed as application No. PCT/KR2010/001999 on Apr. 1, 2010, now abandoned.

(30) Foreign Application Priority Data

Dec. 24, 2009   (KR) ........................ 10-2009-0130834

(51) Int. Cl.
   *A61F 13/36*   (2006.01)
   *A61L 15/28*   (2006.01)
   (Continued)

(52) U.S. Cl.
   CPC ............. *D21H 11/00* (2013.01); *A61F 13/36* (2013.01); *A61F 13/44* (2013.01); *A61L 15/26* (2013.01);
   (Continued)

(58) Field of Classification Search
   CPC ............. A61F 13/36; A61F 2013/00217; A61F 2013/15495; A61F 2013/15869;
   (Continued)

(56) References Cited

U.S. PATENT DOCUMENTS 3,316,906 A * 5/1967 Heinz ............... A61F 13/00059
                                                             604/307
3,808,095 A * 4/1974 McKnight ................. D21F 1/00
                                                             162/131

(Continued)

FOREIGN PATENT DOCUMENTS

DE   68924069 T2   3/1996
DE   69428312 T2   4/2002

(Continued)

OTHER PUBLICATIONS

International Search Report issued by the ISA/KR in connection with PCT/KR2010/001999 dated Feb. 17, 2011.

*Primary Examiner* — Michael A Tolin
(74) *Attorney, Agent, or Firm* — Levenfeld Pearlstein, LLC

(57) ABSTRACT

The present invention relates to a medical nonwoven fabric comprising gelable cellulose derivative short-cut fibers as prepared by the paper making process, a preparation method thereof, and an adhesion prevention barrier using the same. The present invention provides a single phase of medical nonwoven fabric comprising gelable cellulose derivative short-cut fibers, to induce capillary action of micropores formed between the fibers and thereby control the gelation time, and provides a composite nonwoven fabric formed by laminating a nonwoven fabric layer comprising a different kind of biodegradable polymer material not susceptible to gelation on the single-phase of medical nonwoven fabric comprising gelable cellulose derivative short-cut fibers, thereby improving dimensional stability and convenience of (Continued)

surgical procedure. The present invention further provides a dyed medical nonwoven fabric to improve visibility, allowing easiness of recognizing the placement or location of the medical nonwoven fabric.

10 Claims, 7 Drawing Sheets

(51) Int. Cl.
| | |
|---|---|
| A61L 15/60 | (2006.01) |
| D21H 13/04 | (2006.01) |
| D21H 11/00 | (2006.01) |
| D21H 11/20 | (2006.01) |
| A61L 15/56 | (2006.01) |
| A61L 31/04 | (2006.01) |
| A61L 31/12 | (2006.01) |
| A61L 31/14 | (2006.01) |
| D21H 21/28 | (2006.01) |
| A61F 13/44 | (2006.01) |
| D04H 1/407 | (2012.01) |
| D21H 25/04 | (2006.01) |
| D21H 27/30 | (2006.01) |
| D21H 17/37 | (2006.01) |
| D21H 15/02 | (2006.01) |
| D21H 17/36 | (2006.01) |
| D21H 21/18 | (2006.01) |
| A61L 15/26 | (2006.01) |
| D21H 17/24 | (2006.01) |
| D21H 17/53 | (2006.01) |
| D21H 17/25 | (2006.01) |
| D21H 21/52 | (2006.01) |
| A61F 13/15 | (2006.01) |
| A61F 13/00 | (2006.01) |
| D21H 21/14 | (2006.01) |

(52) U.S. Cl.
CPC .............. *A61L 15/28* (2013.01); *A61L 15/56* (2013.01); *A61L 15/60* (2013.01); *A61L 31/042* (2013.01); *A61L 31/048* (2013.01); *A61L 31/129* (2013.01); *A61L 31/146* (2013.01); *D04H 1/407* (2013.01); *D21H 5/1281* (2013.01); *D21H 13/04* (2013.01); *D21H 15/02* (2013.01); *D21H 17/24* (2013.01); *D21H 17/25* (2013.01); *D21H 17/36* (2013.01); *D21H 17/375* (2013.01); *D21H 17/53* (2013.01); *D21H 21/18* (2013.01); *D21H 21/28* (2013.01); *D21H 21/52* (2013.01); *D21H 25/04* (2013.01); *D21H 27/30* (2013.01); *A61F 2013/00217* (2013.01); *A61F 2013/15495* (2013.01); *A61F 2013/15869* (2013.01); *A61F 2013/15951* (2013.01); *D21H 21/14* (2013.01); *Y10T 156/10* (2015.01); *Y10T 442/668* (2015.04); *Y10T 442/669* (2015.04)

(58) Field of Classification Search
CPC .. A61F 2013/15951; A61F 2013/15991; A61F 2013/530036; A61F 2013/530233; A61F 2013/530386; A61L 2/081; A61L 15/225; A61L 15/26; A61L 15/28; A61L 15/60; A61L 15/64; A61L 31/042; A61L 31/048; A61L 31/06; A61L 31/146; C08B 11/12; C08L 1/28; C08L 1/286; D21H 5/1281; D21H 5/141; D21H 5/20; D21H 5/207; D21H 5/2671; D21H 11/00; D21H 11/20; D21H 13/04; D21H 13/24; D21H 17/375; D21H 17/53; D21H 21/28; D21H 25/02; D21H 25/04

See application file for complete search history.

(56) References Cited

U.S. PATENT DOCUMENTS

| 4,651,725 A * | 3/1987 | Kifune ................ A61L 15/225 424/443 |
|---|---|---|
| 5,651,862 A | 7/1997 | Anderson et al. |
| 5,874,100 A | 2/1999 | Mahoney et al. |
| 6,075,177 A | 6/2000 | Bahla et al. |
| 6,123,958 A | 9/2000 | Cheong et al. |
| 2002/0111576 A1 | 8/2002 | Greene et al. |
| 2003/0124310 A1* | 7/2003 | Ellis ........................ B32B 5/04 428/138 |
| 2005/0136769 A1 | 6/2005 | Despault et al. |
| 2009/0280162 A1 | 11/2009 | Wegmann et al. |
| 2010/0129633 A1 | 5/2010 | Law |

FOREIGN PATENT DOCUMENTS

| DE | 69724257 T2 | 7/2004 | |
|---|---|---|---|
| DE | 10318802 A1 | 11/2004 | |
| DE | 60018480 T2 | 2/2006 | |
| EP | 0006647 B1 | 7/1983 | |
| EP | 0227955 A2 | 7/1987 | |
| EP | 0431479 A1 | 6/1991 | |
| EP | 0815879 A2 | 1/1998 | |
| EP | 1378255 A2 | 1/2004 | |
| EP | 1424085 A1 | 6/2004 | |
| EP | 1424087 A1 | 6/2004 | |
| EP | 1430911 A2 | 6/2004 | |
| GB | 2000452 A * | 1/1979 | ............. A61L 15/28 |
| KR | 10-0894377 B1 | 4/2009 | |
| WO | 2007121912 A2 | 11/2007 | |
| WO | 2011078442 A1 | 6/2011 | |

* cited by examiner

MEDICAL NONWOVEN FABRIC, AND PREPARATION METHOD THEREOF

CROSS-REFERENCE TO RELATED APPLICATIONS

This is a divisional application of U.S. application Ser. No. 13/517,356, filed Jun. 20, 2012, now abandoned, which is national stage application of PCT/KR2010/001999, filed Apr. 1, 2010, which claims the benefit of and priority to Korean Patent Application No. 10-2009-0130834, filed Dec. 24, 2009, the contents of each of which are incorporated fully by reference herein.

TECHNICAL FIELD

The present invention relates to a medical nonwoven fabric in the form of a wet-laid nonwoven fabric comprising gelable cellulose derivative short-cut fibers as prepared by the paper making process, a preparation method thereof, and an adhesion prevention barrier using the same and, more particularly to, a medical nonwoven fabric as a single nonwoven fabric, a composite nonwoven fabric improved in dimensional stability and convenience of surgical procedures, and an adhesion prevention barrier using the composite nonwoven fabric, which are prepared by an optimized preparation method improving the strength of the nonwoven fabric.

BACKGROUND ART

Nonwoven fabrics are defined as plane sheet- or web-shaped fabric structures mechanically or physically bonded together by entangling fiber, such as natural fiber, chemical fiber, glass fiber, metal fiber, etc., according to the characteristics of the fiber.

Recently, nonwoven fabrics are widely used in various industrial and home applications and their uses and properties have been increasingly known to the actual demanders, leading to creation of their more different applications.

With many expanded studies made on the applied science as in many developed countries, multifunctional nonwoven fabrics according to high edge technology have recently been progressively introduced and developed in rapid progress.

The nonwoven fabrics applied in the medical field are used as surgical drapes, pads, dressings, filters, or tissue scaffolds implanted for regeneration of internal organs of the body, in addition to surgical gowns, masks, and so forth.

FIG. 1 illustrates the process of preparing a wet-laid nonwoven fabric using the paper making process that involve (1) beating the fibers; (2) dispersion of the fibers in an aqueous medium, which is carried out repeatedly when necessary; (3) web formation on the paper-making wire or screen mesh 31 as a result of filtration and pressing it in the form of a sheet with a vacuum pump 32; (4) passing the web through press rollers to form a wet-laid nonwoven fabric; and (5) winding the wet-laid nonwoven fabric. The sheet thus obtained is made of short-cut fibers, for example, 1 to 7 mm long in water in order to get uniform dispersion of fiber, leading to better uniformity than dry-laid nonwovens.

In an attempt to use wet-laid nonwoven fabrics prepared by the paper making process for medical applications, the inventors of the present invention have found it out that the optimal conditions to improve the strength of nonwoven fabric allows preparation of a medical nonwoven fabric comprising gelable cellulose derivative short-cut fibers and facilitates the control of the gelation time through capillary actions caused by the micropores between the gelable cellulose derivative short-cut fibers, so they have contrived a nonwoven fabric suitable for medical use and further developed a composite nonwoven fabric or a dyed nonwoven fabric with improved dimensional stability and visibility during the surgical procedure using the single-component nonwoven fabric of the present invention, which is also applicable as an adhesion prevention barrier, thereby completing the present invention.

DISCLOSURE OF INVENTION

Technical Problem

It is therefore an object of the present invention to provide a medical nonwoven fabric in the form of a wet-laid nonwoven fabric comprising gelable cellulose derivative short-cut fibers as prepared by the paper making process.

It is another object of the present invention to provide a method for preparing the medical nonwoven fabric comprising gelable cellulose derivative short-cut fibers.

It is still another object of the present invention to provide a method for preparing a medical composite nonwoven fabric with a controlled gelation time on a wet-laid nonwoven fabric comprising gelable cellulose derivative short-cut fibers.

It is further another object of the present invention to provide the medical usage of an adhesion prevention barrier using the medical nonwoven fabric.

Technical Solution

To accomplish the above objects, the present invention is to provide a medical nonwoven fabric using the paper making process.

In accordance with a first preferred embodiment of the present invention, there is provided a medical nonwoven fabric in the form of a wet-laid nonwoven fabric comprising gelable cellulose derivative short-cut fibers. The cellulose derivative short-cut fibers are made of a cellulose derivative prepared from natural cellulose or regenerated cellulose by chemical treatment.

The wet-laid nonwoven fabric comprising short-cut fibers had micropores 1 to 500 µm, preferably 1 to 200 µm, more preferably 1 to 100 µm in size, and can be controlled in gelation time through the capillary action pertaining to the presence of the micropores. The pore size is not specifically limited and may be controlled within the above-defined range according to the usage of the nonwoven fabric.

The medical nonwoven fabric as a single component nonwoven fabric comprising gelable cellulose derivative short-cut fiber may be dyed with a biocompatible dye or pigment.

In accordance with a second preferred embodiment of the present invention, there is provided a medical composite nonwoven fabric comprising a laminate of: a first nonwoven fabric layer in the form of a wet-laid nonwoven fabric comprising gelable cellulose derivative short-cut fibers; and a second nonwoven fabric layer comprising a different kind of biodegradable polymer material not susceptible to gelation.

Here, the composite nonwoven fabric further comprises a dyed layer with a biocompatible dye or pigment to improve visibility during surgical procedures. The dyed layer may be applied to the first nonwoven fabric layer, preferably to the second nonwoven fabric layer.

The wet-laid nonwoven fabric comprising short-cut fibers on the first nonwoven fabric layer has micropores 1 to 500 μm in size to render the gelation time controllable.

The medical composite nonwoven fabric according to the second embodiment of the present invention is provided in the form of a laminate of the first and second nonwoven fabric layers bonded together completely or partially bonded through ultrasound bonding.

The medical composite nonwoven fabric according to the second embodiment of the present invention is a nonwoven fabric using fibers prepared from biodegradable polymer material. The biodegradable polymer material may be a homopolymer of a compound selected from the group consisting of glycolide, glycolic acid, lactide, lactic acid, caprolactone, dioxanone, trimethylene carbonate, and ethylene glycol, or a copolymer comprising the homopolymer. More preferably, the second nonwoven fabric layer comprises a homopolymer or a copolymer prepared from glycolide or glycolic acid.

The medical nonwoven fabric according to the first or second embodiment of the present invention may be applied to any one medical application selected from an adhesion prevention, an air shielding, a hemostat, a cell culturing scaffold, or supporting material for wound closure.

The present invention provides a method for preparing a medical nonwoven fabric that comprises: (1) mixing and dispersing with respect to 100 parts by weight of a cellulose fiber, 0 to 50 parts by weight of a binder material and 0 to 10 parts by weight of a biocompatible dispersing agent as suspended in a aqueous medium under agitation; (2) filtering the mixture to obtain a nonwoven fabric of short-cut fibers; and (3) subjecting the nonwoven fabric to chemical treatment to form a wet-laid nonwoven fabric comprising gelable cellulose derivative short-cut fibers. The preparation method for a medical nonwoven fabric according to the present invention is characterized by adding a dispersing agent to the aqueous medium in order to improve dispersion, and using a binder material in powder or fiber form to improve the strength of the final nonwoven fabric.

In the preparation method for a medical nonwoven fabric, the binder material may be a polymer with a hydroxyl group selected from polyvinyl alcohol or chitosan; or any one polymer selected from the group consisting of homopolymers or copolymers prepared from glycolide, lactide, caprolactone, dioxanone, or trimethylene carbonate.

In the preparation method for a medical nonwoven fabric, the preferred dispersing agent may be any one selected from the group consisting of a poly(ethylene oxide)-(propylene oxide)-based nonionic surfactant, a Tween-series polysorbate surfactant, and polyacrylamide.

Further, a method for preparing a medical composite nonwoven fabric may comprise: positioning a second nonwoven fabric layer comprising a biodegradable polymer material on a first nonwoven fabric layer provided in the form of the wet-laid nonwoven fabric comprising gelable cellulose derivative short-cut fibers; and bonding the first and second nonwoven fabrics together for full lamination by calendering or partial bonding by ultrasound bonding.

The preparation method for a medical composite nonwoven fabric according to the present invention may further comprise conducting a dyeing process on the first nonwoven fabric with a solution containing a biocompatible dye or pigment.

The preparation method for a medical composite nonwoven fabric according to the present invention may further comprise applying gamma radiations after preparation of the second nonwoven fabric layer or the composite nonwoven fabric, to control the biodegradation rate of the biodegradable polymer.

Further, the present invention provides the use of the medical nonwoven fabric or the medical composite nonwoven fabric as an adhesion prevention barrier for preventing adhesion formation between tissues or organs after the surgical procedure.

Advantageous Effects

The present invention can provide a medical nonwoven fabric in the form of a wet-laid nonwoven fabric comprising gelable cellulose derivative short-cut fibers as prepared by the paper making process, and a preparation method for the medical nonwoven fabric that enhances the gelation.

The medical nonwoven fabric of the present invention is a porous thin nonwoven fabric using a biocompatible material and dyed to enhance convenience of surgical procedures.

The present invention can also provide a composite nonwoven fabric made of a dual laminate comprising a gelable cellulose derivative and a biodegradable polymer material not susceptible to gelation, and thereby further provide a preparation method for a medical nonwoven fabric that features easiness of controlling the characteristic of micropores of the nonwoven fabric and simplifies the manufacturing process.

Further, the present invention can provide the use of a single or composite nonwoven fabric comprising gelable cellulose derivative short-cut fibers as an adhesion prevention barrier.

BEST MODE FOR CARRYING OUT THE INVENTION

The present invention will be hereafter described in detail.

The present invention is directed to a medical nonwoven fabric with micropores as provided in the form of a wet-laid nonwoven fabric by the paper making process.

In accordance with the first preferred embodiment of the present invention, the medical nonwoven fabric is provided in the form of a wet-laid nonwoven fabric comprising short-cut fibers of cellulose derivative which are made from natural cellulose or regenerated cellulose by chemical treatment.

Unlike the conventional medical products only with filament fibers or staple fibers, the medical nonwoven fabric of the present invention comprising short-cut fibers prepared by the paper making process can use short-cut fibers made of, for example, natural cellulose as well as regenerated cellulose. The wet-laid nonwoven fabric prepared by the paper making process is more favored in making thin nonwovens and more suitable for medical uses than the nonwovens fabric prepared by the conventional dry method.

Also, the wet-laid nonwoven fabric of the present invention is a porous thin nonwoven fabric with micropores, which induce the capillary action to enhance the gelation. The pore size is not specifically limited, with the provision that it is not greater than 1,000 μm, and the inherent pore size of the nonwoven fabric made of short-cut fiber may be within the range. But, the pore size of the wet-laid nonwoven fabric of the present invention is 1 to 500 μm, which range is preferable for medical uses. The pore size less than 1 μm deteriorates the function of the micropores between fibers to lower the absorption rate, whereas the pore size greater than 500 μm renders the micropores between fibers extremely large even when water causes gelation of the material, readily leading to a deterioration of the barrier property of the nonwoven fabric.

Figure 2:
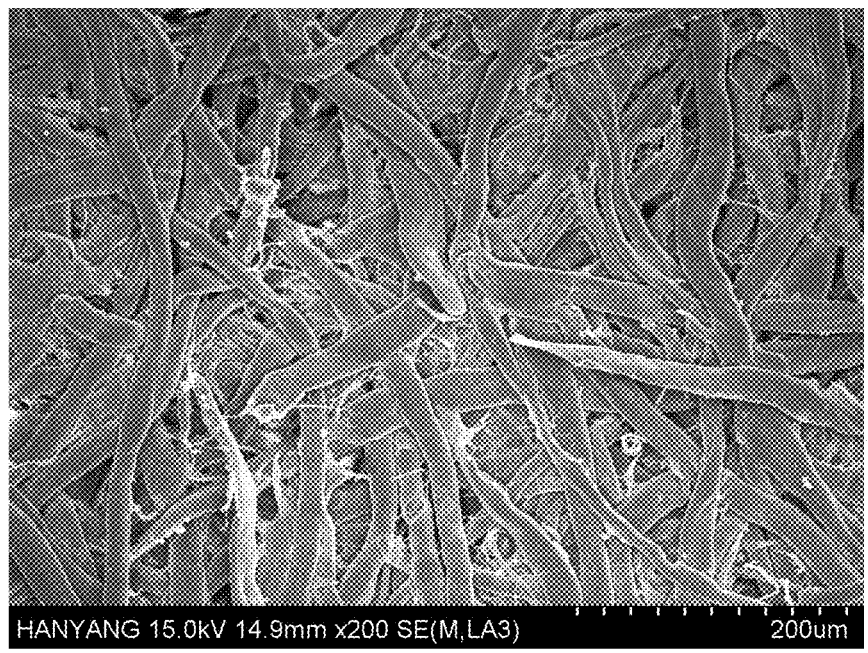
FIG. 2 is a SEM picture showing the surface of a wet-laid nonwoven fabric consisting of short-cut fibers according to Example 1 as a first embodiment of the medical nonwoven fabric of the present invention.
Figure 3:
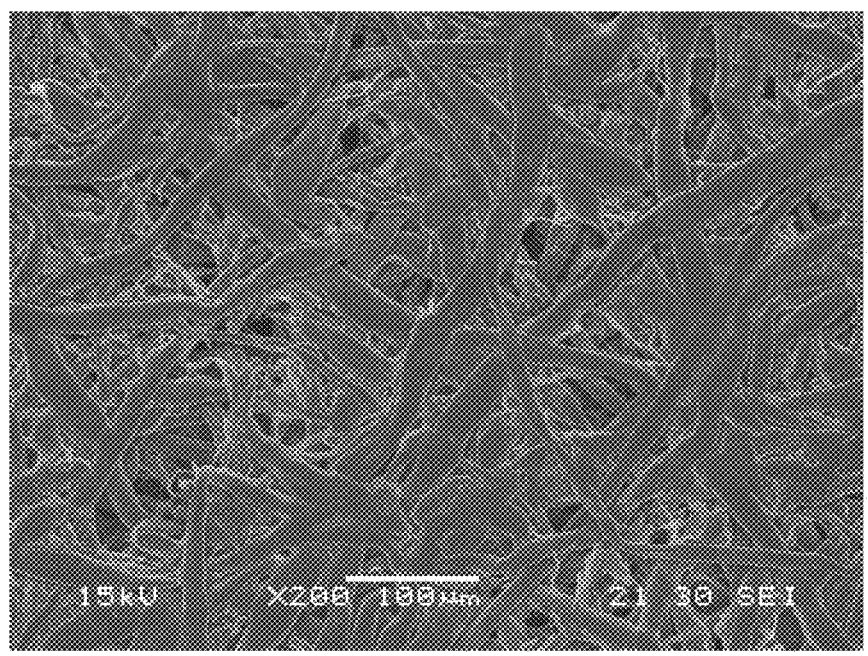
FIG. 3 is a SEM picture showing the surface of a wet-laid nonwoven fabric consisting of short-cut fibers according to Example 2 as the first embodiment of the medical nonwoven fabric of the present invention.
Figure 4:
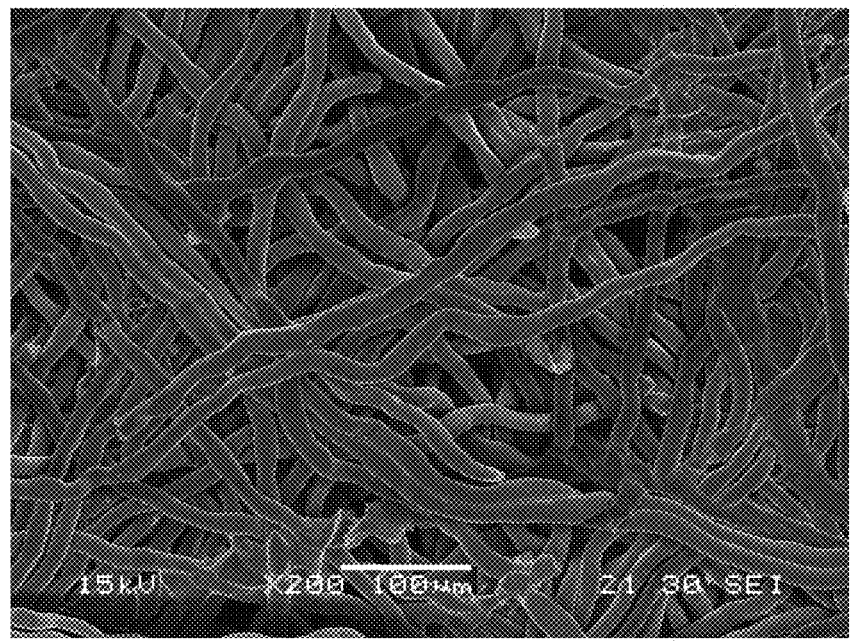
FIG. 4 is a SEM picture showing the surface of a wet-laid nonwoven fabric consisting of short-cut fibers according to Example 3 as the first embodiment of the medical nonwoven fabric of the present invention.

FIG. 2 to FIG. 4 present the SEM pictures showing the surface of the wet-laid nonwoven fabric comprising short-cut fibers prepared in Examples 1, 2 and 3 as the first embodiment of the medical nonwoven fabric of the present invention. More specifically, FIG. 3 and FIG. 4 show that the micropores in the nonwoven fabric using fibrillated fiber of Example 2 are smaller than those in the nonwoven fabric of Example 3 of the same area.

The preferred second embodiment of the present invention provides a medical composite nonwoven fabric comprising a laminate of: a first nonwoven fabric layer in the form of a wet-laid nonwoven fabric comprising gelable cellulose derivate short-cut fibers; and a second nonwoven fabric layer comprising a different kind of biodegradable polymer material not susceptible to gelation.

When the medical nonwoven fabric according to the second embodiment of the present invention is a gelable cellulose derivative nonwoven fabric, it is ready to move during the surgical procedure due to gelation even in the presence of a small amount of water and difficult to handle. To solve this problem, the medical nonwoven fabric according to the second embodiment of the present invention has a composite structure that includes the gelable cellulose derivative material with water in the first nonwoven fabric layer and the biodegradable polymer not susceptible to gelation in the second nonwoven fabric layer.

Thus, the biodegradable polymer used in the second nonwoven fabric layer is preferably a biodegradable polymer not susceptible to gelation in contrast to the gelable cellulose derivative material in the first nonwoven fabric layer. The examples of the biodegradable polymer may include a homopolymer or a copolymer of a compound selected from the group consisting of glycolide, glycolic acid, lactide, lactic acid, caprolactone, dioxanone, trimethylene carbonate, and ethylene glycol.

More preferably, the biodegradable polymer of the second nonwoven fabric layer is a homopolymer or a copolymer prepared from glycolide or glycolic acid.

Figure 5:
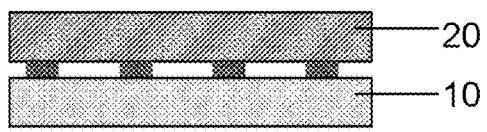
FIG. 5 is a schematic diagram showing the structure of a composite nonwoven fabric prepared by partial bonding as a second embodiment of the medical nonwoven fabric of the present invention.

FIG. 5 is a schematic diagram of a composite nonwoven fabric having a partial bonding structure as the medical nonwoven fabric according to the second embodiment of the present invention. The composite nonwoven fabric of FIG. 5 is of a partial bonding structure having a first nonwoven fabric layer 10 in the form of a wet-laid nonwoven fabric comprising gelable cellulose derivative short-cut fibers; and a second nonwoven fabric layer 20 provided on the first nonwoven fabric layer 10 and comprising a biodegradable polymer material not susceptible to gelation in contrast to the nonwoven fabric material of the first nonwoven fabric layer 10.

Figure 6:
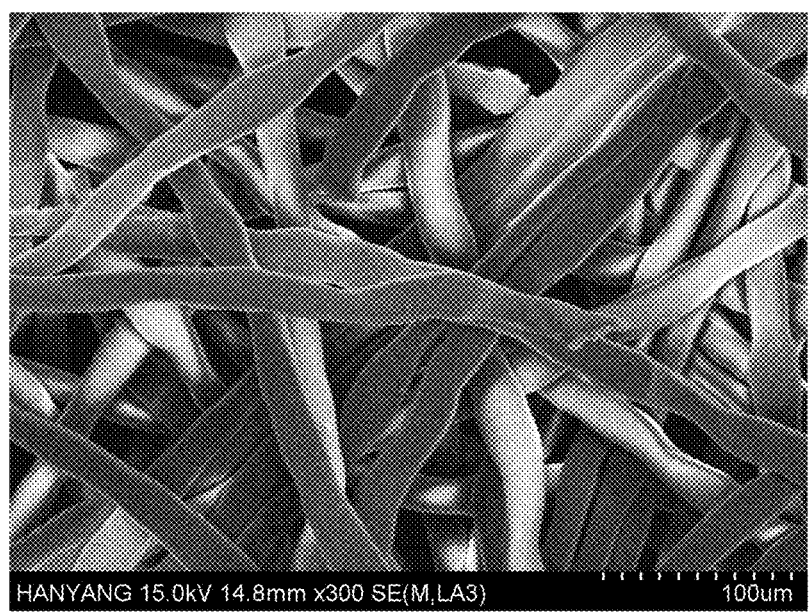
FIG. 6 is a SEM picture showing the surface of a second nonwoven fabric layer according to Example 4 as the second embodiment of the medical nonwoven fabric of the present invention.
Figure 7:
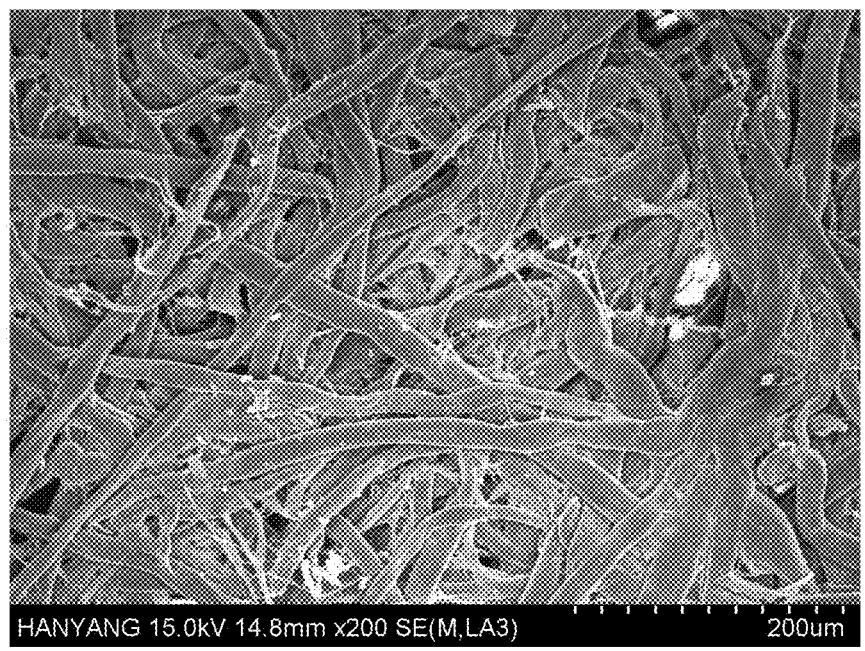
FIG. 7 is a SEM picture showing the surface of a first nonwoven fabric layer according to Example 4 as the second embodiment of the medical nonwoven fabric of the present invention.

For example, the composite nonwoven fabric having a partial bonding structure as prepared in Example 4 is shown in SEM pictures: FIG. 6 shows the surface of a polyglycolic acid (PGA) nonwoven fabric in the second nonwoven fabric layer 20; and FIG. 7 shows the surface of a carboxymethyl cellulose (CMC) nonwoven fabric in the first nonwoven fabric layer 10. As can be seen from the SEM pictures, the first nonwoven fabric layer 10 is provided in the form of a porous nonwoven fabric with micropores to acquire a high gelation speed through the capillary action, while the second nonwoven fabric layer 20 has a porous structure that supports the gelated first nonwoven fabric layer 10 without deteriorating the capillary action of the first nonwoven fabric layer 10, to enhance the dimensional stability before and after the surgical procedure.

Figure 8:
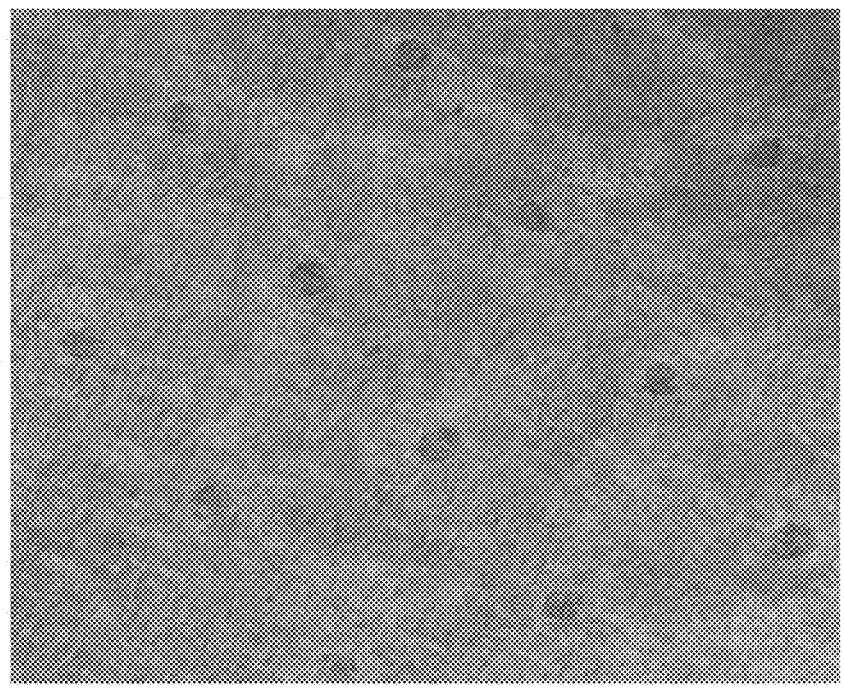
FIG. 8 is a picture showing the surface viewed from the side of the second nonwoven fabric layer according to Example 4 as the second embodiment of the medical nonwoven fabric of the present invention.
Figure 9:
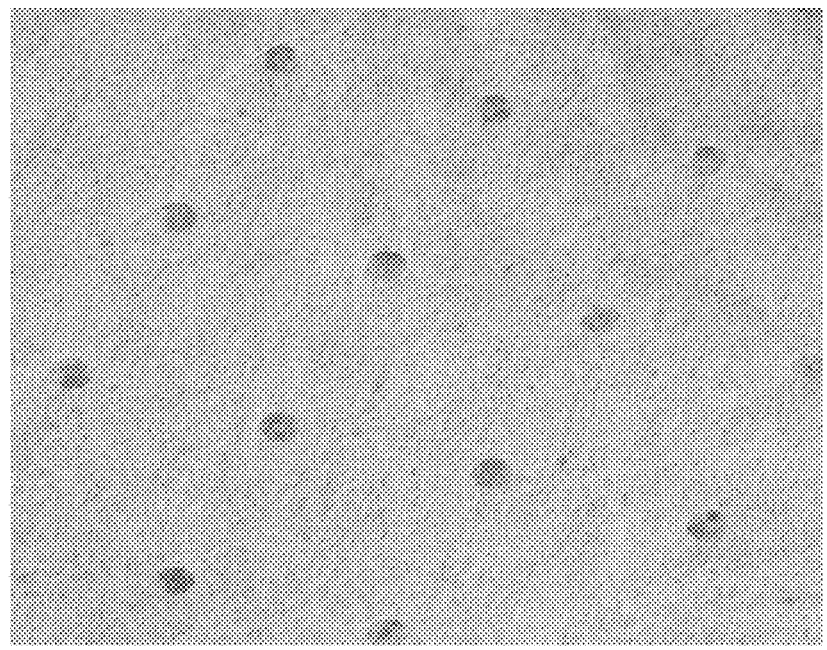
FIG. 9 is a picture showing the surface viewed from the side of the first nonwoven fabric layer according to Example 4 as the second embodiment of the medical nonwoven fabric of the present invention.

FIG. 8 shows the surface of the nonwoven fabric viewed from the side of the second nonwoven fabric layer 20, and FIG. 9 shows the surface of the nonwoven fabric viewed from the side of the first nonwoven fabric layer 10, where the nonwoven fabric is prepared by ultrasound bonding in defined patterns.

Figure 10:
FIG. 10 is a schematic diagram showing the structure of a composite nonwoven fabric prepared by full lamination as the second embodiment of the medical nonwoven fabric of the present invention.
Figure 11:
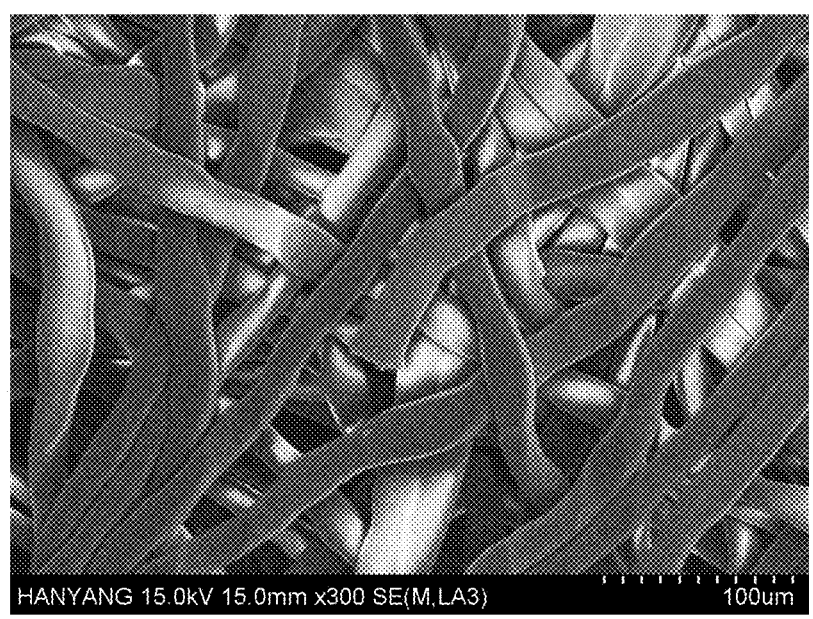
FIG. 11 is a SEM picture showing the surface of a second nonwoven fabric layer according to Example 5 as the second embodiment of the medical nonwoven fabric of the present invention.
Figure 12:
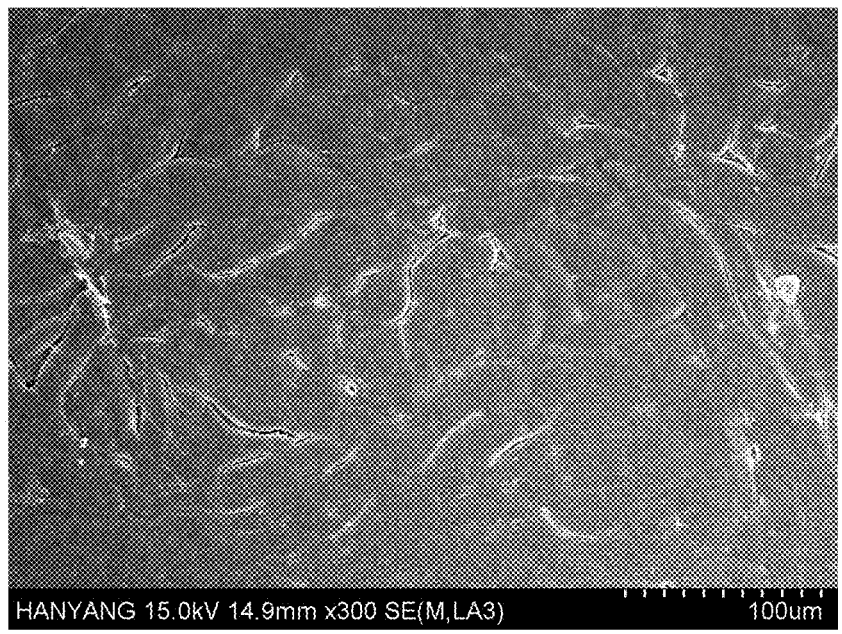
FIG. 12 is a SEM picture showing the surface of a first nonwoven fabric layer according to Example 5 as the second embodiment of the medical nonwoven fabric of the present invention.

FIG. 10 is a schematic diagram of a composite nonwoven fabric having a full laminate structure as another example of the medical nonwoven fabric according to the second embodiment of the present invention. The composite nonwoven fabric has a second nonwoven fabric layer 20 provided on the first nonwoven fabric layer 10 and comprises a different kind of biodegradable polymer material not susceptible to gelation in contrast to the nonwoven fabric material of the first nonwoven fabric layer 10. The composite nonwoven fabric prepared in Example 5 is shown in SEM pictures: FIG. 11 shows the surface of a polyglycolic acid (PGA) nonwoven fabric in the second nonwoven fabric layer 20; and FIG. 12 shows the surface of a carboxymethyl cellulose (CMC) nonwoven fabric in the first nonwoven fabric layer 10. As can be seen from the SEM pictures, the nonwoven fabric has a dense structure almost without micropores, in contrast to the non-laminated single nonwoven fabric of FIG. 4.

In the composite nonwoven fabric according to the second embodiment of the present invention, the first nonwoven fabric layer 10 has micropores formed between gelable cellulose derivative short-cut fibers, leading to fast gelation through the capillary action. The pore size is preferably in the range of 1 to 500 μm, which contributes to an efficient control of the gelation time. Further, the second nonwoven fabric layer 20 comprising a biodegradable polymer material not susceptible to gelation is laminated on the first gelable nonwoven fabric layer 10 with water during the surgical procedure. Such a composite structure can promote the dimensional stability and the convenience of surgical procedure and provide easiness of cutting out the nonwoven fabric in size suitable to the site for the surgical procedure.

When necessary, the second nonwoven fabric layer 20 or the final composite nonwoven fabric in the second embodiment may be exposed to gamma radiations to accelerate the degradation in the body.

Figure 13:
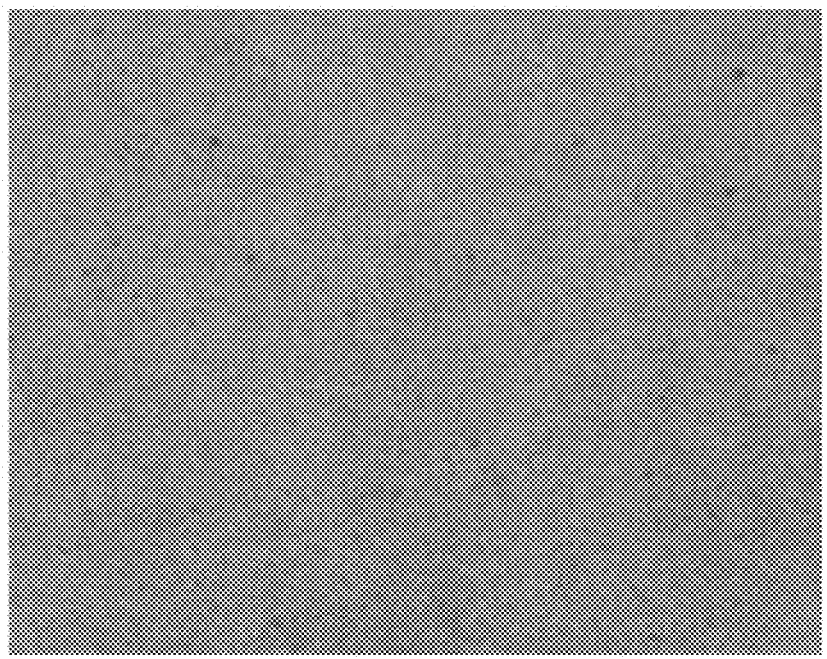
FIG. 13 is a picture showing the surface of a dyed medical composite nonwoven fabric in Example 6 of the present invention.

FIG. 13 is a picture showing the dyed medical composite nonwoven fabric according to the first embodiment of the present invention, where the nonwoven fabric made of a gelable cellulose derivative material is dyed with a biocompatible dye or pigment by a coating method or the like to provide a better convenience of surgical procedure.

The dye or pigment is selected from the biocompatible materials as known in the related art and is preferably of a complementary color to blood for easiness of recognizing the placement or the location of the medical nonwoven fabric in the body after the surgical procedure. The preferred example of the dye or pigment is a violet pigment in the present invention but may not be specifically limited.

The dyed nonwoven fabric of the present invention can enhance the convenience of surgical procedure by overcoming the problem with the conventional medical products which are colorless or white-colored and difficult to recognize their introduction into the body during the surgical procedure. The thickness of the dyed layer is not specifically limited and may be acceptable when it can improve the visibility. Unlike the typical adhesion prevention barriers, the medical nonwoven fabric of the present invention which is a porous thin nonwoven fabric using a biocompatible material is dyed in any color that will enhance the convenience of surgical procedure.

Hence, the medical nonwoven fabric according to the first or second embodiment of the present invention may be used in any one medical application selected from an adhesion prevention barrier, an air shielding, a hemostat, a cell culturing scaffold, or a supporting material for wound closure.

The present invention also provides a method for preparing a medical nonwoven fabric.

Figure 1:
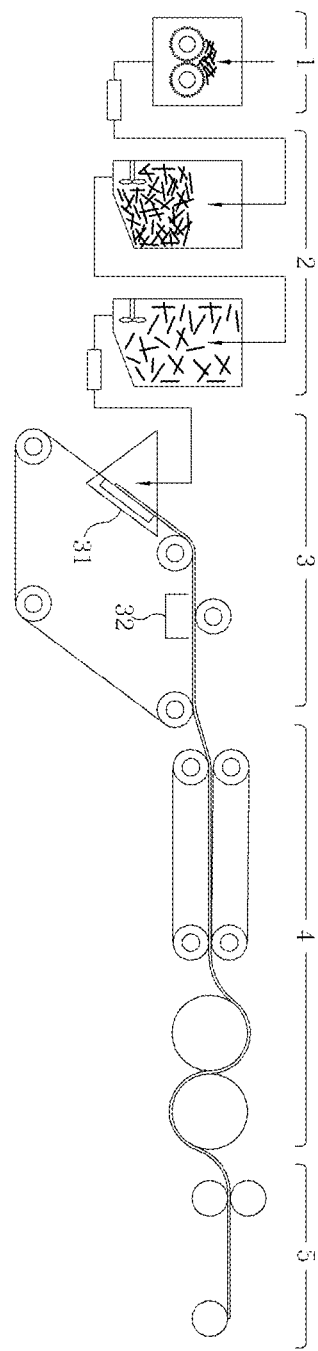
FIG. 1 shows the process of preparing a wet-laid nonwoven fabric using the paper making process.

FIG. 1 shows the process for preparing a wet-laid nonwoven fabric using the paper making process. In the manufacture of a nonwoven fabric from regenerated cellulose fibers by the paper making process, the nonwoven fabric is hard to prepare due to the smooth surface of the fibers and ready to deteriorate in strength, which leads to a demand for improving the strength of the nonwoven fabric.

To render the surface rough, the cellulose fibers are preferably fibrillated before making nonwoven fabric and compressed by calendering.

Another way to enhance the strength of the nonwoven fabric involves adding a binder material. Hence, the preparation method for a medical nonwoven fabric according to the present invention adds an optimal binder material and optimizes the composition for improved dispersion to improve the strength of the nonwoven fabric and thereby to provide a single-phase nonwoven fabric that realizes the dimensional stability.

More specifically, the preparation method for a medical nonwoven fabric comprises: 1) mixing and dispersing, with respect to 100 parts by weight of a cellulose fiber, 0 to 50 parts by weight of a binder material and 0 to 10 parts by weight of a biocompatible dispersing agent as suspended in a aqueous medium under agitation; 2) filtering the mixture of the solvent and compressing the mixture to obtain a nonwoven fabric made of short-cut fibers; and 3) subjecting the nonwoven fabric to chemical treatment to form a wet-laid nonwoven fabric comprising gelable cellulose derivative short-cut fibers.

Preferably, the binder material as used herein is a polymer with a hydroxyl group selected from polyvinyl alcohol or chitosan; or any one polymer selected from the group consisting of a homopolymer or a copolymer prepared from glycolide, lactide, caprolactone, dioxanone, or trimethylene carbonate. The binder material may be used in powder or fiber form.

The binder material is preferably used in an amount of 0 to 50 parts by weight with respect to 100 parts by weight of the cellulose fibers. The content of the binder material greater than 50 parts by weight makes it difficult to cause gelation. More preferably, the nonwoven fabric contains 0 to 10 parts by weight of the binder material with respect to 100 parts by weight of the cellulose fibers.

The composition for enhance the dispersion in the preparation method of a nonwoven fabric may use a biocompatible dispersing agent known in the related art.

The dispersing agent as used herein may be at least one selected from cationic surfactants, anionic surfactants, nonionic surfactants, or amphoteric surfactants. The examples of the cationic surfactants may include alkyl ammoniums (e.g., alkyltrimethyl ammonium or alkyltriethyl ammonium), alkyl dimethyl benzyl ammonium salts, phosphate amine salts, and so forth.

The examples of the anionic surfactants may include alkyl sulphate; alkyl sulfonate; alkyl carboxylic acid; sulphates of polyethoxylated derivatives of linear or branched aliphatic alcohol and carboxylic acid; alkyl benzene or alkyl naphthalene sulfonate or sulphate (e.g., sodium octylbenzene sulfonated); alkyl carboxylate (e.g., dodecylcarboxylate); or alkali metal or (alkyl) ammonium salts of ethoxylated or polyethoxylated alkyl or aralkyl alcohol carboxylate.

The examples of the amphoteric surfactants may include alanines, imidazolium betaines, amide propyl betaines, aminodipropionates, and so forth.

The examples of the nonionic surfactants may include poly(ethylene oxide), (octaethylene glycol)monododecyl ether (C12E08), (octaethylene glycol)monohexadecyl ether (C16E08), a copolymer of poly(ethylene oxide) and poly(propylene oxide), and a triblock copolymer of poly(ethylene oxide), poly(propylene oxide) and poly(alkylene oxide) (e.g., poly(ethylene oxide)-poly(propylene oxide)-poly(ethylene oxide) (PEO-PPO-PEO), or PPO-PEO-PPO).

More preferably, the dispersing agent used in the present invention may be any one selected from the group consisting of a biocompatible poly(ethylene oxide)-(propylene oxide)-based nonionic surfactant, a Tween-series polysorbate-based surfactant, and polyacrylamide. The most preferred example of the dispersing agent in the present invention is, if not specifically limited to, a poly(ethylene oxide)-(propylene oxide)-based nonionic surfactant.

The content of the dispersing agent is preferably 0 to 10 parts by weight with respect to 100 parts by weight of the cellulose fibers.

The present invention provides a method for preparing a medical composite nonwoven fabric that comprises: positioning a second nonwoven fabric layer 20 comprising a biodegradable polymer material on a first nonwoven fabric layer 10 provided in the form of the wet-laid nonwoven fabric comprising gelable cellulose derivative short-cut fibers; and bonding the first and second nonwoven fabrics together for full lamination by calendering.

The present invention also provides another method for preparing a medical composite nonwoven fabric that comprises: positioning a second nonwoven fabric layer 20 comprising a biodegradable polymer material on a first nonwoven fabric layer provided in the form of the wet-laid nonwoven fabric comprising gelable cellulose derivative short-cut fibers; and bonding the first and second nonwoven fabrics together for partial bonding by ultrasound bonding.

The preparation method of a composite nonwoven fabric using a partial bonding by ultrasound bonding is preferred to the preparation method using a full lamination by calendering, because it simplifies the lamination by ultrasound bonding, makes it easier to control the pore properties of the nonwoven fabric and prevents an abrupt decrease in the pore size (See FIG. 5 and FIGS. 6 to 9).

The preparation method for a medical composite nonwoven fabric according to the present invention may further comprise conducting a dyeing process on the first nonwoven fabric with a solution containing a biocompatible dye or pigment. The dyeing process may involve impregnation, coating, or spraying.

More specifically, after preparation of the first nonwoven fabric layer, a dye/pigment (e.g., D&C Violet No. 2, D&C Green No. 6, etc.) together with a biodegradable polymer is applied to the surface of the nonwoven fabric by dipping or coating. In another method, a dyed fiber is used to make the nonwoven fabric layer in the manufacture of a composite nonwoven fabric.

For a controlled biodegradation rate, the preparation method for a medical composition nonwoven fabric according to the present invention may further comprise applying gamma radiations after preparation of the second nonwoven fabric layer or the composite nonwoven fabric.

Further, the present invention provides the use of the medical nonwoven fabric or the medical composite nonwoven fabric as an adhesion prevention barrier.

The adhesion prevention barriers commercially available are provided in knit or film form. The knit type adhesion prevention barrier has the micropores between fibers extremely large that potentially leave an area not blocked even after gelation. Further, the knit type adhesion prevention barrier needs to use long fibers to be prepared in the knit form.

Contrarily, the adhesion prevention barrier using the nonwoven fabric of the present invention uses a wet-laid nonwoven fabric made of short-cut fibers by the paper making process, achieving a controlled pore size unlike the conventional knit type ones.

The film type adhesion prevention barrier, which is free from micropores, lowers the absorption speed pertaining to capillary action. Contrarily, the adhesion prevention barrier using the single-phase nonwoven fabric or the composite nonwoven fabric of the present invention contains micropores between fibers to induce the capillary action, achieving a faster gelation than the conventional film type adhesion prevention barrier.

In particular, the composition nonwoven fabric of the present invention laminates the second nonwoven fabric layer 20 on the first nonwoven fabric layer 10 to promote the dimensional stability of the adhesion prevention barrier during the surgical procedure and convenience of the surgical procedure. Further, unlike the typical adhesion prevention barriers, the adhesion prevention barrier of the present invention is colored to enhance the convenience of the surgical procedure.

Figure 14:
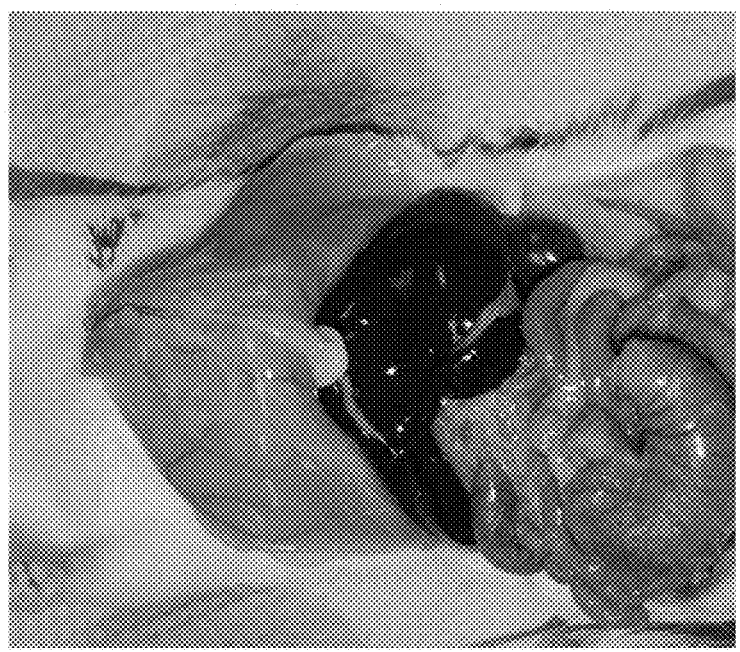
FIG. 14 is a picture showing the adherence result with an adhesion prevention barrier using the nonwoven fabric of the present invention.

FIG. 14 shows that the adhesion prevention barrier using the nonwoven fabric of the present invention is placed in the large intestine of an SD rat after surgical procedure and observed for occurrence of adherence one week after implantation. In FIG. 14, there appears no occurrence of adherence.

Hereinafter, the present invention will be described in further detail with reference to the examples, which are given only for better understanding of the present invention and intended not to limit the scope of the present invention.

[Example 1] Preparation of Nonwoven Fabric Using Natural Cellulose 2.0 g of wood pulp was suspended in 12 L of water to prepare an aqueous mixture under agitation, which was sufficiently dispersed and 50 g/m$^2$ of nonwoven fabric was prepared by a hand sheet former.

The nonwoven fabric thus obtained was subjected to calendering between roll calenders maintained at 170° C. and 500 psi and made into a cellulose nonwoven fabric. The cellulose nonwoven fabric was converted to a carboxymethyl cellulose (CMC) nonwoven fabric through a typical chemical treatment. For the chemical treatment process, 3 g of the cellulose nonwoven fabric was impregnated with a mixed solution containing 400 ml of 2-propanol and 400 ml of ethanol. After impregnated with a solution prepared by adding 36 ml of a 45% (w/v) sodium hydroxide solution to 800 ml of the mixed solution, the cellulose nonwoven fabric was kept under agitation for 15 minutes. Subsequently, the treated cellulose nonwoven fabric was placed on a water bath at 70□ and then suspended in a MCA (monochloroacetic acid)-containing solution under agitation for 15 minutes. Here, the molar ratio of the MCA (monochloroacetic acid) to the cellulose nonwoven fabric was 3:1. After completion of the reaction, the CMC nonwoven fabric was put in 99.5% methanol, neutralized with acetic acid and then stirred for 10 minutes. Again, the CMC nonwoven fabric was washed with 95% ethanol for 5 minutes and then with 99.5% methanol for 10 minutes. The nonwoven fabric was dried at the room temperature and subjected to calendering at the room temperature under the pressure of 500 psi to form the final CMC nonwoven fabric having an average pore size of 6 μm.

[Example 2] Preparation of Nonwoven Fabric Using Natural Cellulose 1.2 g of wood pulp was suspended in 12 L of water to prepare an aqueous mixture under agitation, which was sufficiently dispersed and 30 g/m² of nonwoven fabric was prepared by a hand sheet former.

The nonwoven fabric thus obtained was subjected to calendering between roll calenders maintained at 100☐ and 500 psi and made into a cellulose nonwoven fabric. The cellulose nonwoven fabric was converted to a carboxymethyl cellulose (CMC) nonwoven fabric through the chemical treatment process of Example 1. The CMC nonwoven fabric was subjected to calendering at the room temperature under the pressure of 500 psi to form the final CMC nonwoven fabric having an average pore size of 12 µm.

[Example 3] Preparation of Nonwoven Fabric Using Regenerated Cellulose

To 12 L of water were added 1.08 g of 3 mm-long regenerated cellulose fibers (Tencel, Lenzing Ltd.), 0.12 g of 3 mm-long polyvinyl alcohol fibers as a binding fiber, and 0.4 g of a poly(ethylene oxide)-(propylene oxide)-based nonionic surfactant (Pluronic F 127, BASF) for enhancing dispersion to prepare an aqueous mixture under agitation, which was sufficiently mixed and 30 g/m² of nonwoven fabric was prepared by a hand sheet former. The nonwoven fabric thus obtained was sent to roll calenders for calendering at 170☐ and 500 psi and made into a cellulose nonwoven fabric. The cellulose nonwoven fabric was subjected to a conventional chemical treatment process to form the final CMC nonwoven fabric having an average pore size of 28 µm.

[Example 4] Preparation of Composite Nonwoven Fabric 1

To 12 L of water were added 1.08 g of 3 mm-long polyglycolic acid (PGA) fibers dyed with a biocompatible pigment (D&C Violet No. 2), 0.12 g of PGLA 370 powder, and 0.02 g of polyethylene sorbitan mono-oleate for enhancing dispersion to prepare an aqueous mixture under agitation, which was sufficiently mixed and 30 g/m² of nonwoven fabric was prepared by a hand sheet former. The nonwoven fabric thus obtained was sent to roll calenders for calendering at 150☐ and 500 psi and made into a PGA nonwoven fabric.

The PGA nonwoven fabric and the CMC nonwoven fabric of Example 2 were combined together and subjected to ultrasound bonding with an ultrasound bonding machine using a current of 1.2 A at a rate of 2 m/min, combining only a part of the fabrics in defined patterned.

[Example 5] Preparation of Composite Nonwoven Fabric 2

To 12 L of water were added 1.08 g of 3 mm-long polyglycolic acid (PGA) fibers dyed with a biocompatible pigment (D&C Violet No. 2), 0.12 g of PGLA 370 powder, and 0.04 g of a poly(ethylene oxide)-(propylene oxide)-based nonionic surfactant (Pluronic F 127, BASF) for enhancing dispersion to prepare an aqueous mixture under agitation, which was sufficiently mixed and 30 g/m² of nonwoven fabric was prepared by a hand sheet former.

The PGA nonwoven fabric and the CMC nonwoven fabric of Example 3 were combined together and subjected to calendaring at 150☐ and 500 psi to prepare a composite nonwoven fabric of carboxymethyl cellulose and polyglycolic acid with an average pore size of 10 µm.

[Example 6] Preparation of Dyed Nonwoven Fabric

The CMC nonwoven fabric prepared in Example 1 was dip-coated with a pigment-containing mixed solution prepared by mixing 0.2 wt % of a copolymer (PGLA 370) of glycolide and lactide (30:70 in molar ratio) and 0.03 wt % of a biocompatible pigment (D&C Violet No. 2) in ethyl acetate as a solvent. The dip-coated CMC nonwoven fabric was dried out to complete a dyed CMC nonwoven fabric.

Experiment 1

Figure 15:
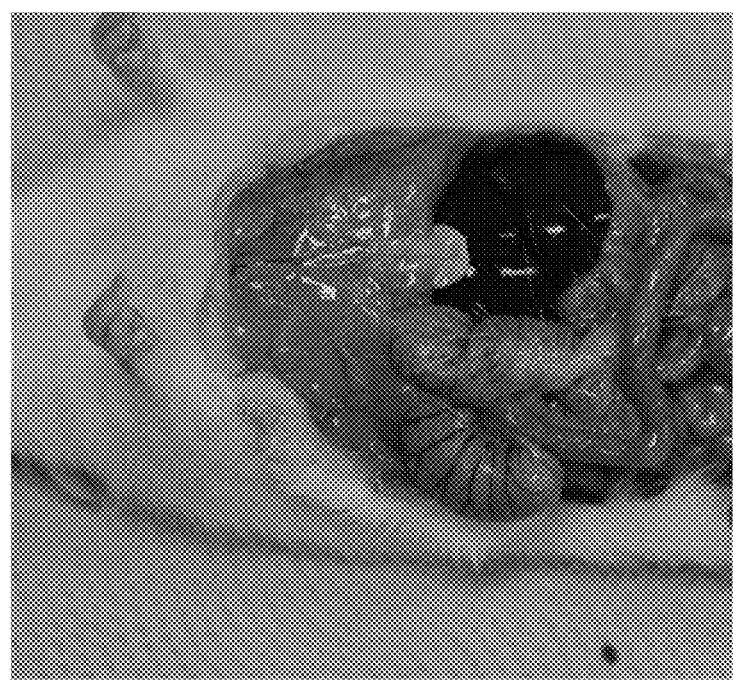
FIG. 15 is a picture showing the adherence result of a control without the adhesion prevention barrier.

The nonwoven fabric prepared in Example 2 was cut in size of 3×3 cm² and the adhesion prevention behavior was evaluated using six to seven-week old SD rats. Firstly, scratches were imposed on the large intestine and the abdominal wall of each SD rat. The control group had no nonwoven fabric placed inside (FIG. 15). The nonwoven fabric prepared in Example 2 (FIG. 14) was placed on the large intestine of each test group and observed in regard to occurrence of post-surgical adhesion one week after implantation. Each test group used five SD rats. The evaluation results are presented in Table 1 and FIGS. 14 and 15.

TABLE 1

| | Adhesion formation | |
| --- | --- | --- |
| Group | Control | Example 2 |
| Adhesion Rate (the number of adhesion/the total number of tests | 5/5 | 0/5 |

As can be seen from the results of Table 1, the adhesion preventive nonwoven fabric of the present invention had no adherence one week after placement. FIG. 14 shows that there appeared no adherence between the large intestine and the abdominal wall one week after placement of the nonwoven fabric of Example 2 on the large intestine. Contrarily, FIG. 15 shows that there was adhesion between the large intestine and the abdominal wall.

INDUSTRIAL APPLICABILITY

As described above, the present invention has beneficial features as follows.

First, the present invention provides a medical nonwoven fabric in the form of a wet-laid nonwoven fabric comprising gelable cellulose derivative short-cut fibers as prepared by the paper making process.

Second, the present invention provides a dyed medical nonwoven fabric, which presents easiness of recognizing the placement and location of an adhesion prevention barrier using the nonwoven fabric during surgical procedure, in contrast to the conventional colorless or white products.

Third, the medical composite nonwoven fabric of the present invention overcomes the problems with the conventional single-phase nonwoven fabric products in regard to gelation of the nonwoven fabric in the presence of water, to improve the convenience of surgical procedure and provide easiness of cutting the nonwoven fabric in size suitable to the site for surgical procedure.

Fourth, the present invention provides a preparation method for a medical nonwoven fabric that makes it easier to control the properties of the micropores in the nonwoven fabric and simplifies the preparation procedure.

Finally, the present invention provides a single-phase nonwoven fabric comprising gelable cellulose derivative short-cut fibers or a multi-layered composite nonwoven fabric including the single-phase nonwoven fabric for use purpose as an adhesion prevention barrier, which contributes to efficient control of the gelation time by way of the capillary action of the micropores formed between the fiber in the nonwoven fabric, in contrast to the conventional knit or film type adhesion prevention barrier.

While the present invention has been described with reference to the particular illustrative embodiments, it is not to be restricted by the embodiments but only by the appended claims. It is immediately apparent that those skilled in the art can change or modify the embodiments without departing from the scope and spirit of the present invention.

The invention claimed is:

1. A method for preparing a medical nonwoven fabric, comprising:

mixing and dispersing a mixture of short-cut cellulose fibers, a binder material, and a biocompatible dispersing agent in an aqueous medium under agitation, wherein the mixture comprises with respect to 100 parts by weight of the cellulose fibers, 0 to 50 parts by weight of the binder material and 0 to 10 parts by weight of the biocompatible dispersing agent;

removing the aqueous medium by filtration and compressing the mixture to obtain a wet-laid nonwoven fabric of short-cut fibers;

calendering the wet-laid nonwoven fabric; and subjecting the wet-laid nonwoven fabric to chemical treatment to form a wet-laid nonwoven fabric comprising gelable cellulose derivative short-cut fibers and having a pore size of 1 μm to 100 μm.

2. The method as claimed in claim 1, wherein the binder material is a polymer with a hydroxyl group selected from the group consisting of polyvinyl alcohol and chitosan; or any one polymer which is a homopolymer or copolymer prepared from a compound selected from the group consisting of glycolide, lactide, caprolactone, dioxanone, and trimethylene carbonate.

3. The method as claimed in claim 2, wherein the binder material is provided in the form of powder or fibers.

4. The method as claimed in claim 1, wherein the biocompatible dispersing agent is any one selected from the group consisting of a poly(ethylene oxide)-(propylene oxide)-based nonionic surfactant, a Tween-series polysorbate surfactant, and polyacrylamide.

5. A method for preparing a medical composite nonwoven fabric, comprising:

manufacturing a first nonwoven fabric layer by performing the method of claim 1;

positioning a second nonwoven fabric layer comprising a biodegradable polymer material not susceptible to gelation on the first nonwoven fabric layer; and bonding the first and second nonwoven fabric layers together by calendering to form the medical composite nonwoven fabric.

6. The method as claimed in claim 5, further comprising:
conducting a dyeing process on the first nonwoven fabric layer with a solution containing a biocompatible dye or pigment.

7. The method as claimed in claim 5, further comprising:
applying gamma radiation to the medical composite nonwoven fabric.

8. A method for preparing a medical composite nonwoven fabric, comprising:

manufacturing a first nonwoven fabric layer by performing the method of claim 1;

positioning a second nonwoven fabric layer comprising a biodegradable polymer material not susceptible to gelation on the first nonwoven fabric layer; and partially bonding the first and second nonwoven fabric layers together by ultrasonic bonding to form the medical composite nonwoven fabric.

9. The method as claimed in claim 8, further comprising:
conducting a dyeing process on the first nonwoven fabric layer with a solution containing a biocompatible dye or pigment.

10. The method as claimed in claim 8, further comprising:
applying gamma radiation to the medical composite nonwoven fabric.

* * * * *